(12) United States Patent
Okada

(10) Patent No.: US 7,404,817 B2
(45) Date of Patent: Jul. 29, 2008

(54) HIGH-FREQUENCY INCISION DEVICE

(75) Inventor: Tsutomu Okada, Tachikawa (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 10/723,820

(22) Filed: Nov. 24, 2003

(65) Prior Publication Data
US 2005/0038424 A1 Feb. 17, 2005

(30) Foreign Application Priority Data
Nov. 25, 2002 (JP) .............................. 2002-341001

(51) Int. Cl.
*A61B 18/18* (2006.01)
(52) U.S. Cl. ...................................................... 606/47
(58) Field of Classification Search ............. 606/27–52, 606/113
See application file for complete search history.

(56) References Cited

U.S. PATENT DOCUMENTS

| | | | | |
|---|---|---|---|---|
| 4,256,113 A | * | 3/1981 | Chamness | 606/47 |
| 4,840,176 A | * | 6/1989 | Ohno | 606/47 |
| 5,263,493 A | * | 11/1993 | Avitall | 607/122 |
| 5,376,094 A | * | 12/1994 | Kline | 606/113 |
| 5,555,883 A | * | 9/1996 | Avitall | 600/374 |
| 5,730,704 A | * | 3/1998 | Avitall | 600/374 |
| 5,897,554 A | * | 4/1999 | Chia et al. | 606/41 |
| 6,093,185 A | * | 7/2000 | Ellis et al. | 606/28 |
| 6,283,988 B1 | * | 9/2001 | Laufer et al. | 607/96 |
| 6,402,740 B1 | * | 6/2002 | Ellis et al. | 606/28 |

FOREIGN PATENT DOCUMENTS

| | | |
|---|---|---|
| JP | 6-217985 | 8/1994 |
| JP | 9-504188 | 4/1997 |
| JP | 10-85230 | 4/1998 |
| JP | 11-1131924 | 4/1999 |

OTHER PUBLICATIONS

Information Sheet for filing an Information Disclosure Statement under Rule 1.56.
Untranslated Japanese Office Action issued on Oct. 30, 2007 in connection with corresponding Japanese application No. 2002-341001.
English translation of Japanese Office Action issued in connection with 2002-341001 submitted in lieu of statement of relevancy of prior art teachings to the instant application.

* cited by examiner

*Primary Examiner*—Roy D. Gibson
*Assistant Examiner*—Pete J Vrettakos
(74) *Attorney, Agent, or Firm*—Ostrolenk, Faber, Gerb & Soffen, LLP

(57) ABSTRACT

A high-frequency incision device includes a high-frequency treating wire 9, which forms a curved portion 11 so that a wire loop 10 formed by the wire 9 may be laterally tilted in a plane parallel to the center axis 7*a* of an actuating wire 7 when the wire 9 extends from the forward end of a flexible sheath 2.

16 Claims, 3 Drawing Sheets

HIGH-FREQUENCY INCISION DEVICE

CROSS-REFERENCE TO RELATED APPLICATIONS

This application is based upon and claims the benefit of priority from the prior Japanese Patent Application No. 2002-341001, filed Nov. 25, 2002, the entire contents of which are incorporated herein by reference.

BACKGROUND OF THE INVENTION

1. Field of the Invention

The present invention relates to a high-frequency incision device for excising tissues in a lumen of a body by being used together with an endoscope.

2. Description of the Related Art

A high-frequency snare has been known as a device to be introduced into a lumen of a body by the use of an endoscope for excising tissues in the lumen. As disclosed, for example, in Jpn. Pat. Appln. KOKAI Publication No. 6-217985, the high-frequency snare includes a conductive wire whose leading end is bent to form an elliptical snare loop, by means of which the tissue in a lumen is bound up tightly, while high-frequency current is passed through the conductive wire, thereby excising or removing the tissue. In such a high-frequency snare, the snare loop has a length in the longitudinal direction longer than the opening width in the transverse direction and its loop surface is positioned on an extension of a center axis of the device.

High-frequency snares have been disclosed in the above Jpn. Pat. Appln. KOKAI Publication and Jpn. Pat. Appln. KOKAI Publication No. 10-85230. In such disclosed devices, in order to facilitate the operation of grasping the tissue present in a zone in front of an endoscope and the incision device, an operation for raising the snare wire is performed to bring the loop plane into a position where the loop plane is intersected by the center line of the endoscope and the incision device.

In recent years, there have been very many clinical reports relevant to lesions spreading transversely to the axial direction of the lumen and lateral spreading tumor (LST) in the field of medical treatment of large intestine.

BRIEF SUMMARY OF THE INVENTION

It is an object of the invention to provide a high-frequency incision device which, is capable of capturing a lesion spread laterally to a sheath by a loop.

The high-frequency incision device of the first aspect according to the invention comprises an elongated sheath having a forward end to be inserted into a lumen of a body and a through-hole opened at the forward end; and an elongated actuating member inserted in the through-hole of the sheath to be movable in its longitudinal direction and having a center axis. The actuating member has at its forward end a high-frequency treating wire extending from the opening at the forward end of the sheath to form a loop having a proximal end and a distal end. When the wire extends from the front end of the sheath, a loop plane of the loop formed by the wire is substantially parallel to the center axis of the actuating member, and the loop laterally extends from the center axis so that a loop center axis connecting the distal end and the proximal end of the loop may be tilted to the center axis of the actuating member.

The high-frequency incision device thus constructed may easily capture the lesion such as even lateral spreading tumor which spread transversely to the axial direction of a lumen.

Preferably, the loop is tilted maintaining a relation of $D1 \geqq D2$, where $D1$ is a length of the loop in a direction perpendicular to the center axis of the actuating member, and $D2$ is a length of the loop in a direction parallel to the center axis of the sheath.

In such a high-frequency incision device, since the width of the wire loop in the transverse direction becomes larger than its length in the longitudinal direction, it becomes possible to more easily capture the lesion such as even the lateral spreading tumor.

The actuating member described above may be preferably bent at a plurality of locations along its center axis. In order to cause such bending, the actuating member may be provided with a linear portion or portions deformable to be bent, or the sheath may be provided with a curved portion causing the actuating member to be bent, or the former and the latter features may be used together.

In the high-frequency incision device, the tilted angle of the laterally extending loop may be selected to be various angles.

BRIEF DESCRIPTION OF THE SEVERAL VIEWS OF THE DRAWING

The accompanying drawings, which are incorporated in and constitute a part of the specification, illustrate of the invention, and together with the general description given above and the detailed description of the embodiments given below, serve to explain the principles of the invention.

DETAILED DESCRIPTION OF THE INVENTION

First Embodiment

The high-frequency snare 1 as a high-frequency incision device of the first embodiment according to the invention will be explained with reference to FIGS. 1 to 3.

Figure 1:
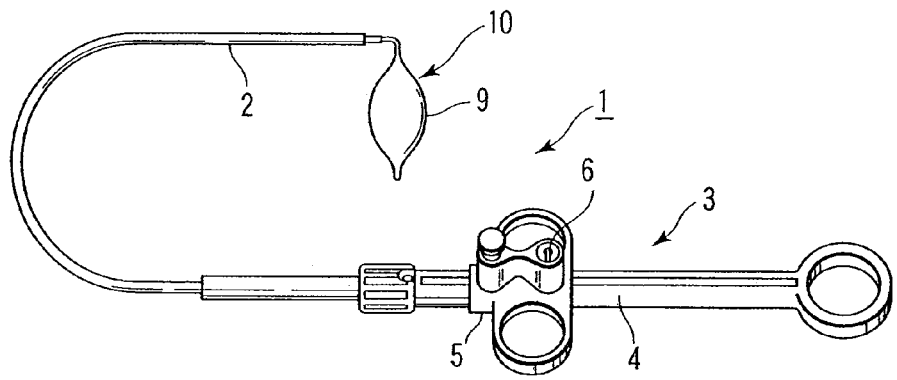
FIG. 1 is a perspective view of the entire high-frequency snare according to the first embodiment of the invention.

FIG. 1 illustrates the high-frequency snare 1 of the first embodiment of the invention. The high-frequency snare 1 comprises a flexible sheath 2 having a through-hole, formed of an insulating material, for example, a synthetic resin, and an actuating portion 3 provided on the side of the proximal end of the flexible sheath 2. The actuating portion 3 comprises a proximal portion 4 whose forward end is connected to the proximal end of the flexible sheath 2, and a slider 5 mounted on the proximal portion 4 axially slidable relative thereto. The slider 5 is provided with an electrode 6 to be connected to a high-frequency power source (not shown) for supplying high-frequency electric current. The electrode 6 is electrically and mechanically connected to the proximal end of an actuating wire 7 as actuating means passing through the through-hole of the flexible sheath 2 extensively and retractably.

Figures 2A, 2B:
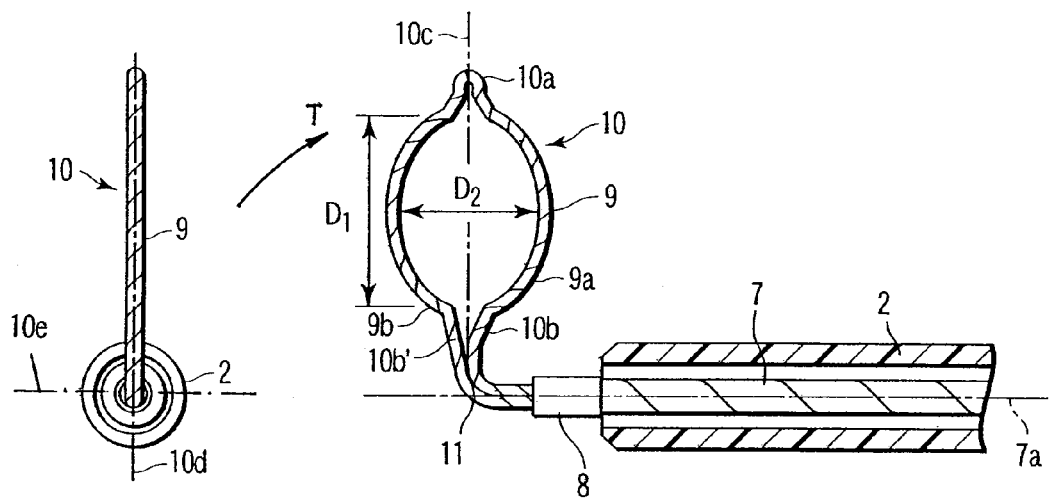
FIG. 2A is an enlarged longitudinal sectional view of the forward end of the high-frequency snare in FIG. 1.
FIG. 2B is a front view of the forward end of the high-frequency snare.

As shown in FIG. 2A, a connection tip 8 is mounted on the forward end of the actuating wire 7 and serves to connect both the ends of a conductive incision wire 9 curved to form a loop as high-frequency treating section to the forward end of the actuating wire 7. There is a tendency of the incision wire 9 imparted to itself to spread outwardly into a ioop by itself owing to its elasticity. Therefore, when in the flexible sheath 2, the incision wire 9 is forced to be straight by the inner surface of the flexible sheath 2. When the incision wire 9 extends from the flexible sheath 2, the incision wire 9 will form a loop 10 owing to the elastically restoring force of itself as shown in FIG. 2A. The loop 10 is formed by two incision wire portions 9a and 9b equal in length formed by folding it at the center therebetween. The loop 10 includes an elliptical ring portion curved with a predetermined curvature and a non-circular ring portion extending from the proximal end of the elliptical ring portion and progressively being narrowed (a substantially triangular ring in the illustrated embodiment). As shown in FIG. 2A, the elliptical ring portion has a length D1 in the transverse direction and a length D2 in the longitudinal direction. The shape of the loop with regard to the relation between the lengths D1 and D2 is set up so as to be D1.gtoreq.D2 when the loop 10 is bent and extends in the transverse direction. In the case that the loop is elliptical and bent at right angles to the center axis 7a as shown in FIG. 2A, the lengths D1 and D2 correspond to or substantially coincide with major and minor axes D1 and D2 of the ellipse. The wire portions 9a and 9b unite with each other at the proximal ends 10b and 10b' of the wire portions forming the non-circular ring portion, while at the united point, that is, at wire portions in the proximity of the proximal end of the incision wire 9, a curved portion 11 is formed. By providing the curved portion 11, the loop 10 of the incision wire 9 extending from the forward end of the flexible sheath 2 can be laterally tilted in the direction of arrow T at a predetermined angle, for example, 90° as shown in FIG. 2A. Laterally tilted presumes rotation centered on a tilting axis 10e (FIG. 2B) generally perpendicular to the plane 10d containing the loop 10. The center axis 10c of the loop is a line connecting the leading end (apex) 10a of the loop 10 which is the center of the folded wire and the center point between the proximal ends 10b and 10b'. The center axis 10c of the loop 10 and the center axis 7a of the actuating wire 7 intersects at a predetermined angle. For example, as shown in the drawing these center axes 10c and 7a intersect at right angles, while the center axis 10c of the loop 10 is at right angles to the center axis 7a of the actuating wire 7 in the plane 10d containing the loop 10.

In the above incision wire 9, the lengths of the incision wire portions 9a and 9b on both sides from the leading end 10a of the loop 10 to the connection tip 8 are substantially equal, but the curved shapes of the proximal ends 10b and 10b' forming the non-circular ring portion are formed in asymmetry, with the result that the (arcuate) shapes of the incision wire portions 9a and 9b formed by the elliptical ring portions of the loop 10 are maintained in symmetry with respect to the center axis 10c.

When the incision wire 9 is drawn into the through-hole of the flexible sheath 2, the incision wire 9 abuts against the forward end face or inner surface of the flexible sheath 2 to be elastically deformed so that the curved portion 11 disappears or becomes straight. When the incision wire 9 is further drawn into the through-hole of the flexible sheath 2, the loop 10 is also collapsed into an elongated shape by the forward end face or the inner surface of the flexible sheath 2. As a result, the incision wire 9 can be received or stored in the flexible sheath 2. From this condition, when the incision wire 9 is extended from the flexible sheath 2, the incision wire 9 will expand or deploy into a loop shape by itself and will bend at right angles at the curved portion 11, so that the loop 10 occupies the lateral position. At this time, the center axis 7a of the actuating wire 7 is positioned on the loop plane 10d formed by the loop 10 as shown in FIG. 2B (Although the center axis 7a is positioned on an extension of the loop plane 10d more exactly, the plane including the extended plane is referred to as "loop plane" in the present invention).

Figure 3:
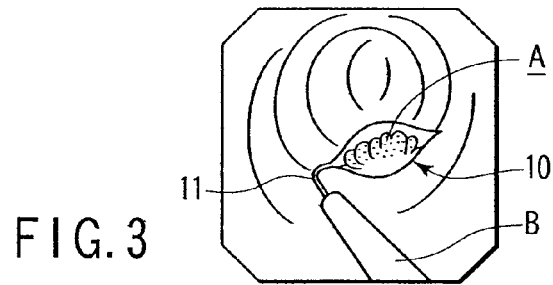
FIG. 3 is an observation view through an endoscope illustrating a state of treating for excising lesions spread laterally in a lumen using the high-frequency snare.

The procedure for excising a laterally extending lesion A in a lumen as shown in FIG. 3, using the high-frequency snare 1 thus constructed will then be explained.

First, the flexible sheath 2 of the high-frequency snare 1 is inserted through an endoscope into a lumen of a patient. When the lesion A is found by an observation using the endoscope B, the slider 5 of the actuating portion 3 is advanced to the proximal portion 4. The incision wire 9 thus extends from the forward end of the flexible sheath 2 so that the loop 10 is formed by the extended incision wire 9 and the loop 10 is tilted onto the lateral side with the aid of the curved portion 11 as shown in FIG. 3. As the center axis 7a of the actuating wire 7 is in the loop plane 10d of the loop 10, the lesion A can be readily captured in the loop 10 of the incision wire 9, even if the lesion A spreads laterally in the lumen viewed from the endoscope B as shown in FIG. 3. In other words, the lesion A can be brought into the loop 10. Thereafter, the slider 5 is retracted to the proximal portion 4 of the actuating portion 3 to draw the incision wire 9 into the flexible sheath 2, with the result that the loop 10 of the incision wire 9 progressively contracts starting from its proximal end to constrict the lesion A. Under this constricted condition, high-frequency electric current flows in the incision wire 9 to excise or cut out the lesion A by the high-frequency electric current.

Now, the loop 10 of the incision wire 9 is curved substantially at right angles to the center axis 7a at the curved portion 11 so that the relation between longitudinal and transverse axes of the loop is reversed, whereby the width in the transverse direction becomes larger than the length in the longitudinal direction. Moreover, as the loop plane 10d and the center axis 7a of the actuating wire 7 coincide with each other, the lesion A can be easily captured in the loop 10 of the incision wire 9, even with the lesion A spread laterally in the lumen viewed from the endoscope B as shown in FIG. 3. In the case capturing laterally spread lesion A in the lumen, the snare according to the invention is particularly preferable.

While the center axis 7a of the actuating wire 7 is in the loop plane 10d defined by the loop 10 in the embodiment, it will be apparent that the loop plane 10d and the center axis 7a of the actuating wire 7 may be separated from and in parallel with each other. Such a feature can be realized in a manner that the proximal ends 10b and 10b' in FIG. 2A are once bent vertically to the plane of the drawing and the loop 10 is then bent so as to be parallel to the plane of the drawing. The expression "the loop plane and the center axis of the actuating wire are in parallel with each other" as used in the present invention is to be understood to include both the cases that the loop plane and the center axis of the actuating wire coincide with, and are separated from each other as described above.

Second Embodiment

Figure 4:
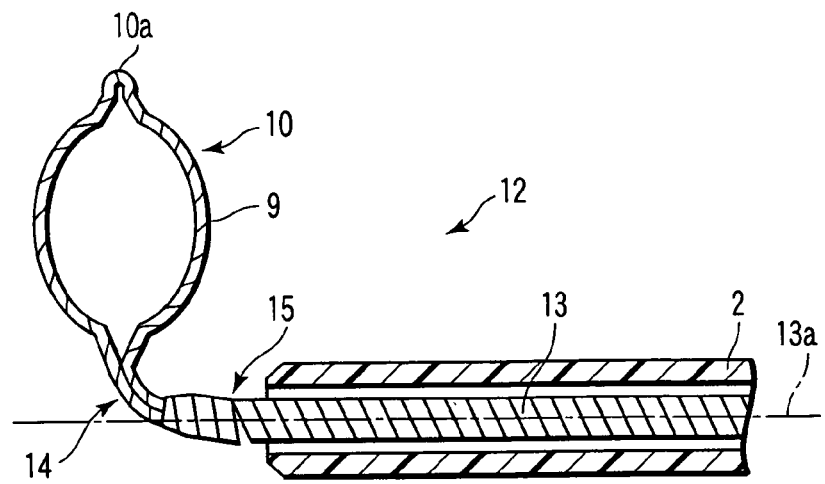
FIG. 4 is an enlarged longitudinal sectional view illustrating the forward end of the high-frequency snare of the second embodiment according to the invention.

The high-frequency snare 12 as high-frequency incision device of the second embodiment of the invention will be explained with reference to FIGS. 4 and 5.

The high-frequency snare 12 of the present embodiment uses an actuating coil 13 densely coiled as actuating means having a transmission faculty of turning force instead of the actuating wire in the first embodiment. Moreover, an incision wire 9 is provided at the proximal end with a curved portion 14 more gradually curved (with a smaller bent angle) than that in the first embodiment. The actuating coil 13 has a comparatively more resistance to bending than a single wire and is provided at its forward end with a second curved portion 15 curved in the same direction as that of the first curved portion 14. As a result, when the incision wire 9 extends from the forward end of the flexible sheath 2, the incision wire 9 is bent to the center axis 13a of the actuating coil 13 at an angle which is a sum of the bent angles of the first and second curved portions 14 and 15. In the illustrated embodiment, bent angles of the first and second curved portions 14 and 15 are approximately 45°, respectively so that the incision wire 9 is bent substantially at right angles to the center axis 13a of the actuating coil 13 onto one lateral side. These individual bent angles and the total bent angle may be arbitrarily determined. Other features are substantially the same as those in the first embodiment.

Figures 5A, 5B:
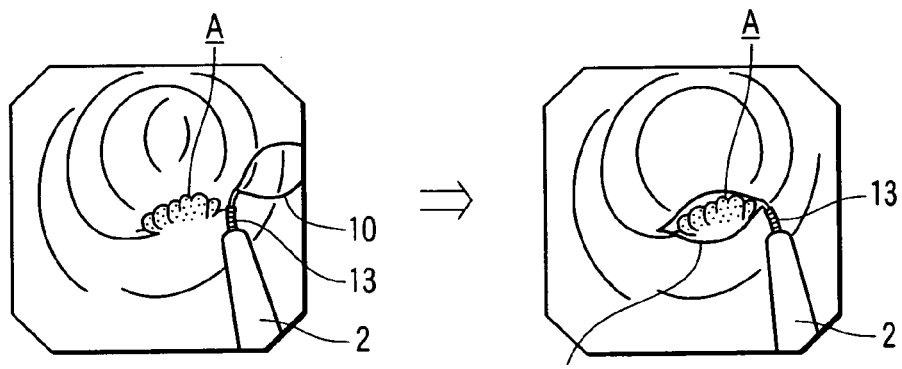
FIGS. 5A and 5B are observation views through an endoscope illustrating different states of treating for excising lesions spread laterally in a lumen using the high-frequency snare of the second embodiment, respectively.

The function of the high-frequency snare 12 of the embodiment will then be explained. As shown in FIG. 5A, when the incision wire 9 extends from the forward end of the flexible sheath 2, if the loop 10 extends onto the opposite side of a lesion A in a lumen, the loop 10 is turned onto the side of the lesion A by turning the actuating coil 13 through 180° by actuating its proximal end so as to permit the loop 10 to be adapted for the lesion A.

According to the high-frequency snare 12 of the second embodiment, when the incision wire 9 is drawn into the flexible sheath 2, only a slight force is required because the incision wire 9 is easily bent at the two curved portions 14 and 15 gradually curved, which is an effect of the second embodiment other than those of the first embodiment described above. Moreover, by turning the actuating coil 13, the loop 10 can be advantageously adapted for the position of a lesion A by changing the extending direction of the loop 10. The functions and effects other than these are substantially the same as those of the first embodiment.

Third Embodiment

Figure 6:
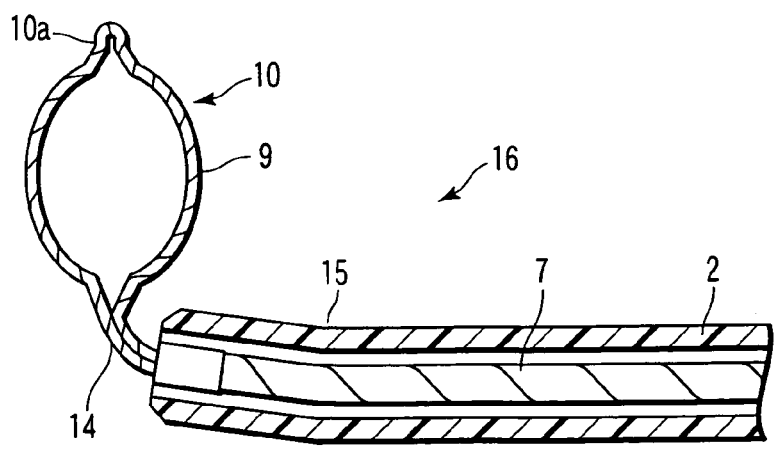
FIG. 6 is an enlarged longitudinal sectional view illustrating the forward end of the high-frequency snare of the third embodiment of the invention.

The high-frequency snare 16 as high-frequency incision device of the third embodiment of the invention will be explained with reference to FIG. 6.

In the high-frequency snare 16 of the third embodiment, the forward end of a flexible sheath 2 affords a functional equivalent to that of the second curved portion 15 of the second embodiment described above. In more detail, the forward end of the flexible sheath 2 is bent at a predetermined angle in the third embodiment, whereas the flexible sheath 2 is substantially straight in the second embodiment. When an actuating wire 7 passes through such a flexible sheath 2, the actuating wire 7 will follow the second curved portion 15 so as to be bent, so that a loop 10 of a incision wire 9 can extend substantially at right angles with the center line 7a of the actuating wire 7 with the aid of the curved portion of the actuating wire 7 caused by the second curved portion 15 and further the first curved portion 14 of the incision wire 9. Other features of the third embodiment are substantially the same as those of the first embodiment. The functions and effects of the third embodiment are substantially the same as those of the first embodiment.

Fourth Embodiment

The high-frequency snare 17 as high-frequency incision device of the fourth embodiment of the invention will be explained with reference to FIGS. 7 to 9.

The high-frequency snare 17 of the fourth embodiment includes an actuating coil 13 as actuating means similar to the actuating coil 13 in the second embodiment. Moreover, an incision wire 9 is formed at it proximal end with a first curved portion 14 more gradually curved than that of the second embodiment, and further the actuating coil 13 is formed at its forward end with second and third curved portions 15 and 18 spaced from each other and more gradually curved than that of the second embodiment. The number of these curved portions may be more than three and bent angles may be equal to or different from one another.

Figure 7:
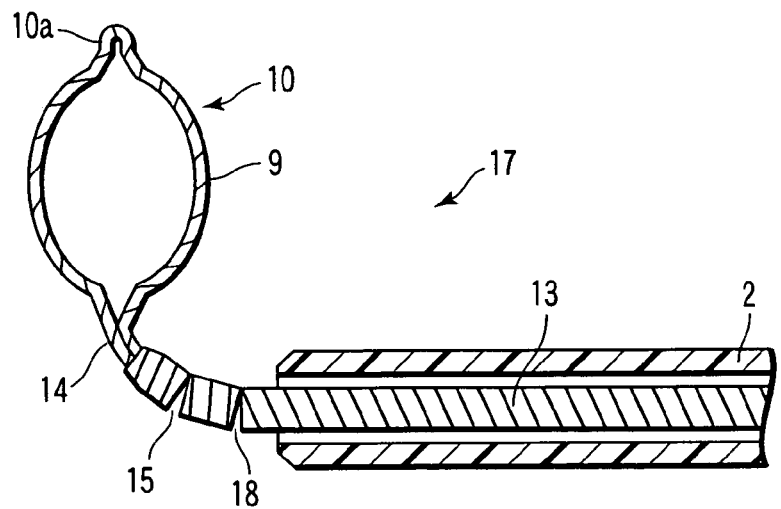
FIG. 7 is an enlarged longitudinal sectional view illustrating the forward end of the high-frequency snare of the fourth embodiment of the invention.

In such a high-frequency snare, when all the curved portions 14, 15 and 18 extend from the forward end of the flexible sheath 2, the portion in the proximity of the proximal end of the incision wire 9 is gradually curved over the substantially long range so that the loop 10 of the incision wire 9 laterally extends at the maximum angle of 90° (first curved condition) as shown in FIG. 7.

Figure 8:
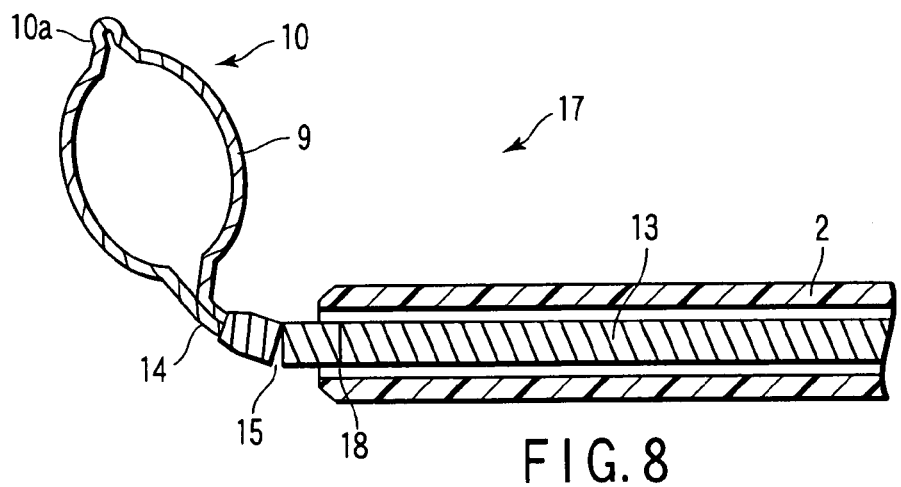
FIG. 8 is an enlarged longitudinal sectional view illustrating another operating condition of the forward end of the high-frequency snare of the fourth embodiment of the invention.

As shown in FIG. 8, moreover, in the state that the curved portions 14 and 15 extend from the flexible sheath 2 and the third curved portion 18 only remains in the flexible sheath 2, the curved portion 18 is straight so that the loop 10 extends at a smaller angle than 90° with the center axis 7a of the actuating coil 13, at substantially 60° or more in this case (second curved condition).

Figure 9:
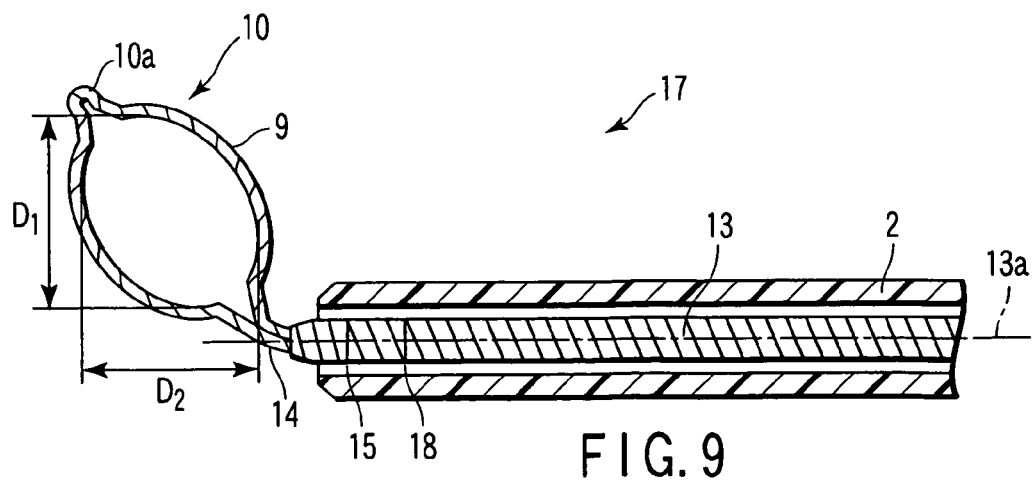
FIG. 9 is an enlarged longitudinal sectional view illustrating a further operating condition of the forward end of the high-frequency snare of the fourth embodiment of the invention.

As shown in FIG. 9, furthermore, in the state that the curved portion 14 only extends from the flexible sheath 2, and the third curved portion 18 and even the second curved portion 15 remain in the flexible sheath 2, the third curved portion 18 and even the second curved portion 15 are straight so that the loop 10 extends at a much smaller angle, substantially 45° in this case (third curved condition).

In this manner, the laterally extending angle of the loop 10 of the incision wire 9 can be gradually and stepwise changed and can be continuously adjusted by selecting the curved portions 14, 15 and 18.

As shown in FIG. 9, when the incision wire 9 extends from the flexible sheath 2 in the lateral direction at a predetermined angle, it is assumed that the lateral width of the loop 10 as a length in the transverse direction (length in the direction perpendicular to the center axis 13a of the actuating coil 13) is D1, and the length of the loop 10 in the longitudinal direction (length parallel to the center axis 13a of the actuating coil 13) is D2. When the loop 10 of the incision wire 9 is laterally tilted to the center axis 13a of the actuating coil 13 by moving it, the position of the loop 10 of the incision wire 9 will be stepwise and gradually changed within the range from the first curved condition to the third curved condition in a manner such that the relation between D1 and D2 becomes $D1 \geq D2$.

The other features of the fourth embodiment are substantially similar to those of the second embodiment. In the fourth embodiment, moreover, even if a lesion A is obliquely inclined, the actuating coil 13 is moved to the flexible sheath 2 so as to permit the curved angle of the loop 10 to adapt for the lesion A so that the lesion A can be easily captured in the loop 10. Further, as the position of the loop 10 of the incision wire 9 can be changed maintaining the relation of $D1 \geq D2$, the capture of a lesion A into the loop 10 becomes easy. The fourth embodiment can bring about the-functions and effects other than these, which are similar to those of the second embodiment of the invention.

Although the loop of the high-frequency snare in the embodiments of the invention is illustrated and explained to be an elliptical or circular ring, it is to be understood that without being limited only to such a shape, any other shapes may be used such as rectangular, rhombic and triangular. Moreover, the elongated actuating member having a wire for high-frequency treating is constructed by a combination of an incision wire and an actuating wire or actuating coil, the constitution, combination and materials are not limited to those explained in the embodiments. While the loop is formed by the elastic restoring force of the material forming the actuating member in the embodiments, it will be apparent that the loop may be formed by other means.

The high-frequency snare according to the invention may be carried out in the following manner.

(1) A high-frequency incision device comprises a sheath to be inserted into a lumen of a body, actuating means provided in the sheath movably in its axial direction, and a high-frequency treating portion formed by a wire provided at the forward end of the actuating means and extending from the forward end of the sheath to form a loop, and the loop being curved at an angle with the axis of the actuating means in a plane containing the axis of the actuating means.

(2) In the high-frequency snare described in (1), the curved loop has a length D1 in the direction perpendicular to the axis of the actuating means (length in the transverse direction) and a length D2 in the axial direction (length in the longitudinal direction) in a relation of $D1 \geq D2$.

(3) In the high-frequency snare described in (1), the angle at which the loop is curved is at right angles (90°).

(4) In the high-frequency snare described in (1), the curved portion forming the curve is provided at the proximal end of the loop.

(5) In the high-frequency snare described in (1), the curved portion forming the curve is provided at the forward end of the actuating means.

(6) In the high-frequency snare described in (4), the curved portion forming the curve is provided at the forward end of the sheath.

(7) The high-frequency snare described in (1) or (2) comprises at least three curved portions described above and means for making the curved portions straight so as to permit the curved angle of the loop to be stepwise adjustable.

The high-frequency snare described in (1) to (6) has the object to facilitate the operation of capturing a laterally spread lesion, and as the longitudinal and transverse axes of the loop can be reversed, the object can be accomplished.

The high-frequency snare described in (7) has the object to make possible to move the loop depending upon a somewhat tilted lesion, and the curved angle of the loop can be stepwise adjusted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic treatment apparatus comprising:
   an elongated sheath having a distal end portion and a through-hole which has an opening at the distal end portion;
   an elongated actuating member having a central axis, a distal end portion, and at least one elastic deformable portion provided at the distal end portion thereof, the actuating member being inserted into the through-hole of the sheath and movable relative to the sheath;
   a treatment section for performing a high-frequency treatment, connected to the elastic deformable portion of the actuating member, the treatment section being laterally extendable for forming a loop when the treatment section is extended from the opening of the sheath by movement of the actuating member, the loop having a distal end, a proximal end, a loop central axis connecting the distal and proximal ends thereof, the loop being symmetric with respect to the loop central axis, and a loop plane including the loop central axis, the loop plane being substantially parallel with a moving axis of the actuating member;
   the proximal end of the loop comprising first and second curved proximal ends connecting the loop to the elastic deformable portion, the first and second curved proximal ends being asymmetric with respect to the loop central axis,
   wherein the ioop central axis of the loop is tilted against the moving axis of the actuating member at a tilting angle, by elastic deformation of the elastic deformable portion due to an inherent elastically restoring force, when the treatment section and distal end of the actuating member are extended from the opening of the sheath.

2. The endoscopic treatment apparatus according to claim 1, wherein the loop is tilted while maintaining a relation of $D1 \geq D2$ where D1 is a length of the loop in a direction perpendicular to the center axis of the actuating member, and D2 is a length of the loop in a direction parallel to the center axis of the sheath.

3. The endoscopic treatment apparatus according to claim 1, wherein the loop central axis is maintained in substantially parallel or aligned with the central axis of the actuating member where the elastic deformable portion is positioned in the through-hole of the sheath.

4. The endoscopic treatment apparatus according to claim 3, wherein the distal end portion of the sheath is bent against the central axis thereof towards a tilting direction of the loop.

5. The endoscopic treatment apparatus according to claim 1, wherein said at least one elastic deformable portion includes a plurality of elastic deformable portions provided along the central axis of the actuating member.

6. The endoscopic treatment apparatus according to claim 1, wherein the tilting angle is substantially 90°.

7. The endoscopic treatment apparatus according to claim 1, wherein the loop central axis of the loop is tilted so that the distal end of the loop is extended toward a direction of the elastically restoring force of the elastic deformable portion, when the treatment section is extended from the opening of the sheath.

8. An endoscopic treatment apparatus comprising:

an elongated sheath which is to be inserted into a body cavity, and having an elongated direction, the sheath having a distal end portion and a through-hole which extends in the sheath along the elongated direction, the distal end portion having an opening communicating with the through-hole;

an elongated actuating member which is inserted into the sheath to be movable relative to the sheath in the longitudinal direction thereof, the actuating member having a central axis, a distal end portion, and at least one elastic deformable portion provided at the distal end portion thereof;

a treatment section connected to the elastic deformable portion of the actuating member, the treatment section being expandable for forming a ioop which is laterally extended against the central axis of the actuating member by an elastic deformation of the elastic deformable portion by an inherent elastically restoring force, when the treatment section is extended from the opening of the sheath by movement of the actuating member; a loop central axis connecting a distal end and a proximal end of the loop being kept to be substantially parallel or aligned with the central axis of the actuating member, when the treatment section is positioned in the through-hole of the sheath, the loop being symmetric with respect to the loop central axis;

the proximal end of the loop comprising first and second curved proximal ends connecting the loop to the elastic deformable portion, the first and second curved proximal ends being asymmetric with respect to the loop central axis; and the loop central axis is tilted against a moving axis of the actuating member, and a loop plane including the loop central axis is generally parallel with the moving axis of the actuating member.

9. The endoscopic treatment apparatus according to claim 8, wherein the loop central axis of the loop is tilted at 90°0 relative to the central axis of the actuating member, when the elastic deformable portion is extended from the opening of the sheath.

10. The endoscopic treatment apparatus according to claim 8, wherein the loop is extended toward a direction of the elastically restoring force of the elastic deformable portion, when the treatment section is extended from the opening of the sheath.

11. An endoscopic treatment apparatus comprising:

an elongated sheath having a distal end portion and a through-hole which has an opening at the distal end portion;

an elongated actuating member having a central axis, a distal end portion, and at least one elastic deformable portion provided at the distal end portion thereof, the actuating member being inserted into the through-hole of the sheath and movable relative to the sheath;

a treatment section connected to the elastic deformable portion of the actuating member, the treatment section being laterally extendable for forming a loop when the treatment section is extended from the opening of the sheath by movement of the actuating member, the loop having a distal end, a proximal end, a loop central axis connecting the distal and proximal ends thereof, and a loop plane including the loop central axis, the loop being synunetric with respect to the loop central axis, the loop plane being substantially parallel with a moving axis of the actuating member;

the proximal end of the loop comprising first and second curved proximal ends connecting the loop to the elastic deformable portion, the first and second curved proximal ends being asymmetric with respect to the loop central axis, wherein the loop central axis of the loop is tilted against the moving axis of the actuating member at a tilting angle, by elastic deformation of the elastic deformable portion due to an inherent elastically restoring force, when the treatment section and distal end of the actuating member are extended from the opening of the sheath.

12. The endoscopic treatment apparatus according to claim 11, wherein the loop is tilted while maintaining a relation of D1≧D2 where D1 is a length of the loop in a direction perpendicular to the center axis of the actuating member, and D2 is a length of the loop in a direction parallel to the center axis of the sheath.

13. The endoscopic treatment apparatus according to claim 11, wherein the loop central axis is maintained in substantially parallel or aligned with the central axis of the actuating member where the elastic deformable portion is positioned in the through-hole of the sheath.

14. The endoscopic treatment apparatus according to claim 13, wherein the distal end portion of the sheath is bent against the central axis thereof towards a tilting direction of the loop.

15. The endoscopic treatment apparatus according to claim 11, wherein said at least one elastic deformable portion includes a plurality of elastic deformable portions provided along the central axis of the actuating member.

16. The endoscopic treatment apparatus according to claim 11, wherein the tilting angle is substantially 90°.

* * * * *